(12) United States Patent
Jeanguillaume

(10) Patent No.: US 6,342,699 B1
(45) Date of Patent: Jan. 29, 2002

(54) MULTI HOLES COMPUTERIZED COLLIMATION FOR HIGH SENSITIVITY RADIATION IMAGING SYSTEM

(76) Inventor: Christian Jeanguillaume, 40 rue de Boissy, Sucy en Brie (FR), 94370

( * ) Notice: Subject to any disclaimer, the term of this patent is extended or adjusted under 35 U.S.C. 154(b) by 0 days.

(21) Appl. No.: 09/307,430

(22) Filed: May 10, 1999

(51) Int. Cl.[7] ............................................. G01T 1/166
(52) U.S. Cl. .............................. 250/363.1; 250/363.04; 250/370.11
(58) Field of Search .................... 250/363.1, 363.04, 250/370.11

(56) References Cited

U.S. PATENT DOCUMENTS

| | | |
|---|---|---|
| 3,011,057 A | 11/1961 | Anger |
| 5,448,073 A | 9/1995 | Jeanguillaume |

FOREIGN PATENT DOCUMENTS

| | | | |
|---|---|---|---|
| FR | 9806061000 | 11/1998 | |
| JP | 54-102184 | * 8/1979 | .............. 250/363.1 |

* cited by examiner

*Primary Examiner*—Constantine Hannaher
*Assistant Examiner*—Andrew Israel (57) ABSTRACT

A high sensitivity radiation imaging system, aimed to perform sections (or tomographic) images of emitted radiation. This system includes a collimator having at least two openings in which the narrowest cross-section is greater than twice the intrinsic resolution of the detector so that different points of radiation impact can be detected in each opening. The plurality of openings differs in shapes, dimensions or orientations in order to provide a better overlap of their impulse function in the Fourier space. The camera head is displaced by successive steps, the successive steps being of the order of magnitude of a predetermined image resolution. Information collected by the detector is processed by storing locating information corresponding of the impact points for each position of the openings during displacement, and processing the information to reconstruct the radiation volume density function. The combination of the various impulse functions related to the different openings allows a full coverage of the Fourier space, thus resulting in high resolution of reconstructed images. This resolution is then independent of the size of the holes allowing the use of large openings resulting in a high sensitivity.

20 Claims, 9 Drawing Sheets

MULTI HOLES COMPUTERIZED COLLIMATION FOR HIGH SENSITIVITY RADIATION IMAGING SYSTEM

BACKGROUND OF THE INVENTION

1. Field of Endeavor to which the Invention Pertains

The present invention relates to radiation detectors and, more particularly, to a radioactivity distribution detection system which has cross section openings larger than the intrinsic resolution of the detector and at least two openings of different shape.

2. Description of Prior Art

Various types of radioactivity distribution detection systems have become known in the art for determining the location of radioactive material injected in diagnostic amounts into a human or an animal body. These systems based on the gamma camera of the Anger type (U.S. Pat. No. 3,011,057) have proven to be of limited sensitivity (10-4) and limited resolution compared to the intrinsic resolution of the detector. Moreover the use of such systems to realize tomography degrades further the spatial resolution of the system. The purpose of tomography is to realize sections of the object emitting the radiation. Tomography of an object emitting gamma rays is also called single photon emission tomography (SPECT). SPECT is different from positron emission tomography (PET) where two photons are simultaneously emitted by the radionuclid. This property permits a coincidence detection, without collimator. The subject of the present invention is a tomographic imaging system able to give a section of the radiation emitter whatever the radiation emitted. This system applies well to gamma rays but it can also apply to X-rays, UV, IR any photons or small particles like neutrons, electrons, or any radiation travelling in straight lines. We proposed to increase the bore hole of the collimator beyond the value of the intrinsic resolution of the detector, and to add a scanning movement of the collimator, in order to get sufficient data (U.S. Pat. No. 5,448,073 Jeanguillaume September 1995). Although this system provides an improvement compared to the conventional system the noise limits slightly the resolution and the accuracy of the reconstructed images. The time of the reconstruction program is another limitation of the system.

BRIEF SUMMARY OF THE INVENTION

It is the object of the present invention to provide some improvements of the high sensitivity gamma camera proposed in the U.S. Pat. No. 5,448,073 C. Jeanguillaume September 1995. The principal improvement is to associate at least two openings of different shape in the collimator, which allows a more complete knowledge of the data to be acquired, and a fast deconvolution algorithm to be performed. A better image and a faster reconstruction time can then be achieved. Another improvement is to describe different physical arrangements to realize the scanning movement necessary to the system. The practical arrangements of linear and orbital movement described herein provide a faster and more complete acquisition.

BRIEF DESCRIPTION OF THE SEVERAL VIEWS OF THE DRAWING

FIG. 3a shows the collimator hole at various scanning positions in front of the point source. FIG. 3b illustrates the detector response for the detector positions given in FIG. 3a. FIG. 3c illustrates the detector response for a complete set of detector scanning positions.

FIG. 4a shows the collimator hole at various scanning positions in front of the point source. FIG. 4b illustrates the detector response for the detector scanning positions given in FIG. 4a. FIG. 4c illustrates the detector response for a complete set of detector scanning positions.

FIG. 5 aims to illustrate the response of the system to two point sources and the shift and sum process.

DETAILED DESCRIPTION OF THE INVENTION

As the improvements are closely linked to almost every part of the prior invention a complete but brief description of the prior invention is necessary. Furthermore the benefits of the improvements will be clear once the description of the prior invention is given (e.g. in FIGS. 8,9).

The prior invention (U.S. Pat. No. 5,448,073 September 1995 C Jeanguillaume) relates to radiation detectors, it aims to show the distribution of radiation emitters through a patient body or any other source of radiation. The Anger camera belongs to the same kind of device (U.S. Pat. No. 3,011,057 November 1961 H Anger). The high sensitivity radiation imaging system differs from the Anger camera by a collimator with larger diameter holes plus a scanning movement. A reconstruction program taking a full account of the depth dependent response function is also a peculiarity.

Figure 1:
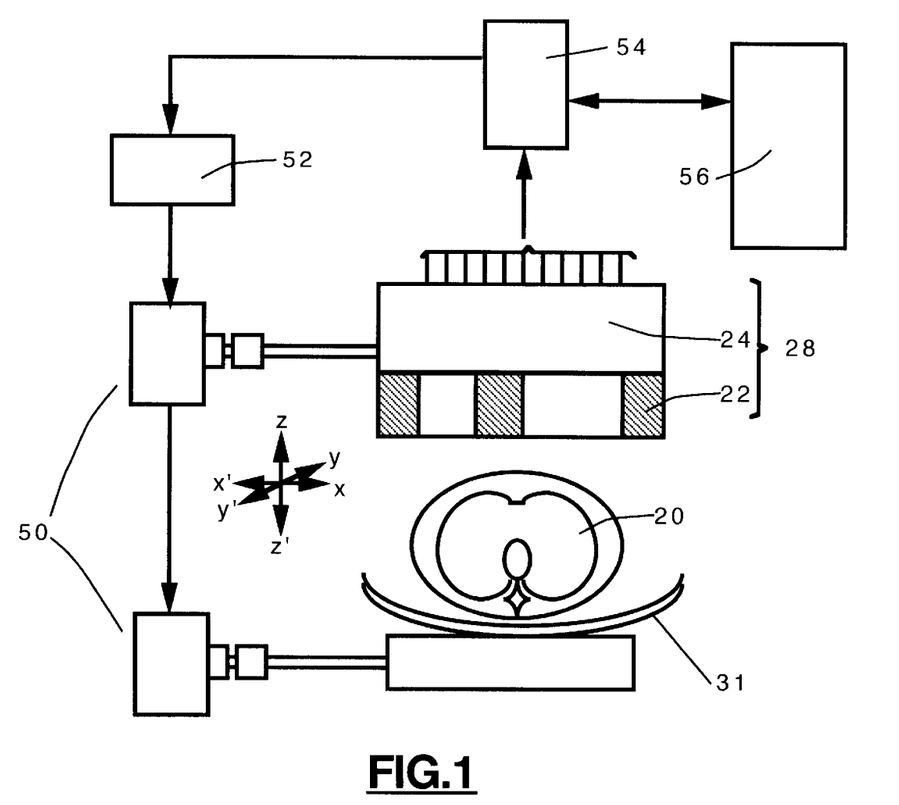
FIG. 1 is a schematic view of the high sensitivity radiation imaging system whose improvement is the subject of the present invention. The source of radiation (object) 20 emits radiation which is detected by a position sensitive detector 24.

FIG. 1 is a schematic view of the high sensitivity radiation imaging system. The patient or source 20 is placed on a table 31. The camera head 28 is composed of a collimator 22 next to a position sensitive detector 24. A position sensitive detector means a detector which can detect an impinging radiation and determines where this radiation has interacted with the detector. The information related to the position of the radiation in the form of electric signals is then transmitted to a computer 54 in order to reconstruct the section of the distribution of radiation source (tomogram) which can be visualized on a screen 56. The computer 54 conducts the scanning movement of the camera head 28 and of the examination table 31 by way of an electronic interface 52, engines and gantry 50. This scanning movement takes place in a the three dimensional space (x,y,z).

The purpose of FIGS. 2 to 7 is to explain briefly the algorithm and the principle of image reconstruction. For the sake of clarity a simplified collimator with only one hole is depicted and the scanning movement is limited to a simple linear motion. An orbital or circular movement although not compulsory is also added to diminish the attenuation effect and to show how it can be incorporated in the reconstruction program.

Figure 2:
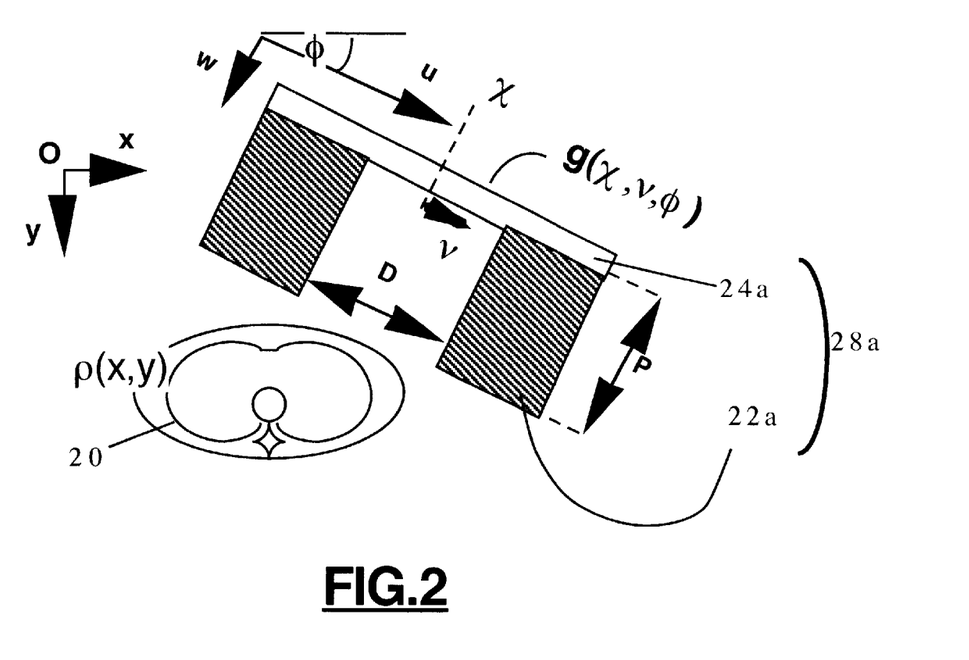
FIG. 2 is a schematic view of a 2D reduction of the problem with a simplified one hole collimator aimed at defining the variables used in the explanation of the method of reconstruction.

FIG. 2 represents a section of the source of radiation 20 and a simplified camera head 28a with a simple collimator with only one hole 22a. We focus our attention on the reconstruction of a section of the emissive object 20 acquired by the linear (1D) detector 24a. $\rho(x,y)$ is the density function to be reconstructed. $\chi,\phi$ are the variables determining the position of the detector in the plane during the circular movement $\phi$ and the linear scanning movement $\chi$. The axes x,y are fixed in the plane while the axes u,w rotate during the acquisition. $\chi$ measures the center of the detector on the u axis and v measures the position of the radiation impact on the detector. P is the depth of the collimator hole, D is its diameter. The relation between the acquisition $g(\chi,u,\phi)$ and the object $\rho$ can be written, with few approximations:

$$g(\chi, v, \phi) = \int_P^\tau \int_{\chi+v-(w/p)(v+D/2)}^{\chi+v-(w/p)(v-D/2)} \frac{\cos\theta}{d2} \rho(x, y) du dw$$

$\rho(x,y)=\rho(u\cos\phi+w\sin\phi, -u\sin\phi+w\cos\phi)$

Where $\cos\phi$ represents the inclination of the impinging radiation referred to the detector surface and d the distance between the source and the detector at the radiation impact.

Figure 3:
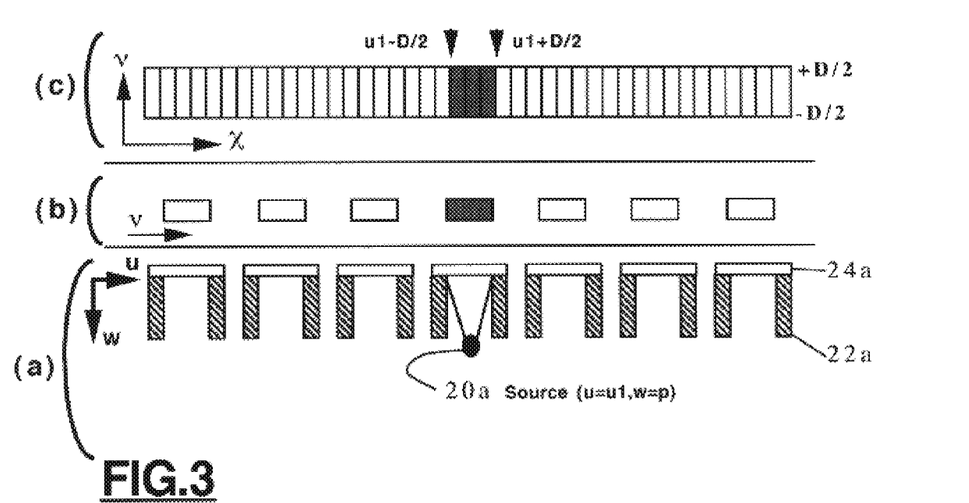
FIG. 3 is a schematic view of the response of the system to a point source situated near the entrance plane of the collimator.

FIG. 3 represents an acquisition for a point source 20a situated near the entrance plane of the collimator 22a. The figure is divided into three parts: a,b,c from the bottom to the top. FIG. 3 Part a shows the collimator hole 22a and the detector 24a at various scanning positions (e.g. various values of $\chi$) in front of the point source 20a. FIG. 3 Part b illustrates the detector response for the detector scanning positions given in FIG. 3 Part a, a shaded portion of the detector means an illuminated detector while a white portion of the detector means no radiation detected. FIG. 3 Part c illustrates the detector response for a complete set of detector scanning positions in the plane $\chi,v$. Note that the detector direction v has been rotated by 90° from FIG. 3 Part b to FIG. 3 Part c. The response in the plane $\chi,v$ has a rectangle shape between the abscissa $u_1-D/2$ and $u_1+D/2$.

Figure 4:
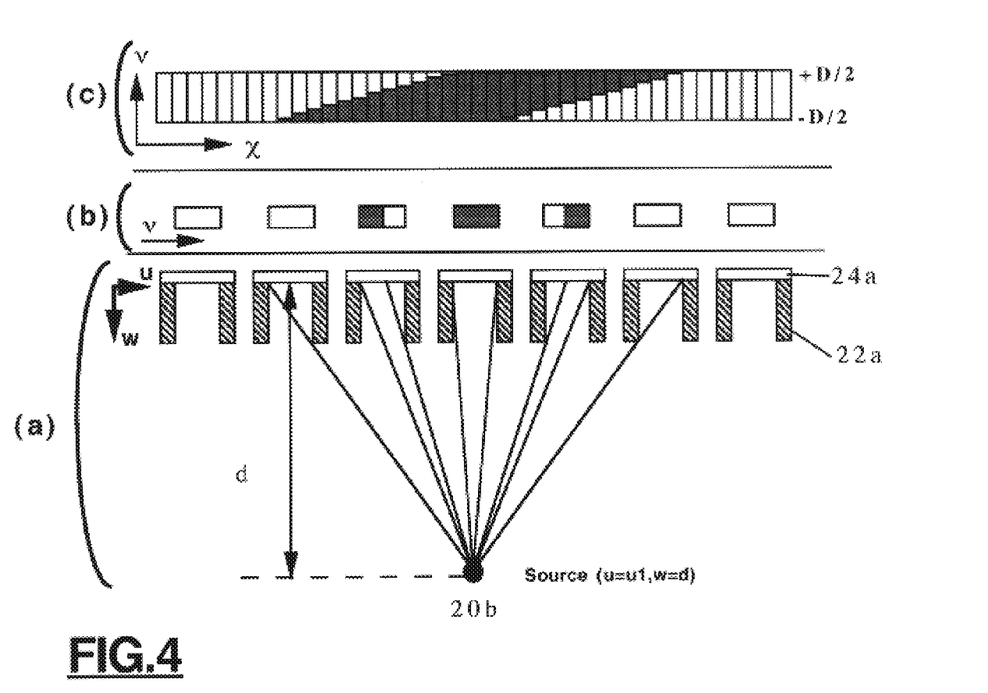
FIG. 4 is a schematic view of the response of the system to a point source situated far from the entrance plane of the collimator.

FIG. 4 is a schematic view of the response of the system to a point source 20b situated far from the entrance plane of the collimator 22a. FIG. 4 Part a shows the collimator hole 22a and the detector 24a at various scanning positions (e.g. various values of $\chi$ ) in front of the point source 20b. FIG. 4 Part b illustrates the detector response for the detector scanning position given in FIG. 4 Part a, a shaded portion of the detector means an illuminated detector while a white portion of the detector means no radiation detected. FIG. 4 Part c illustrates the detector response for a complete set of detector scanning positions in the plane $\chi,v$. Note that the detector direction v has been rotated by 90° from FIG. 4 Part b to FIG. 4 Part c. The response in the plane $\chi,v$ has a parallelogram shape.

The shift and sum process consists on a shift of the data g formalized by the variable change: $g(\chi,v,\phi)->>G(u,v,w)$, and then a sum. G on the v variable to give the function S.

$$\begin{Vmatrix} v - > v \\ \chi - > u = \chi + v((w/P) - 1) \end{Vmatrix}$$

$$S(u, w) = \int_{-D/2}^{+D/2} G(u, v, w) dv$$

Figure 5:
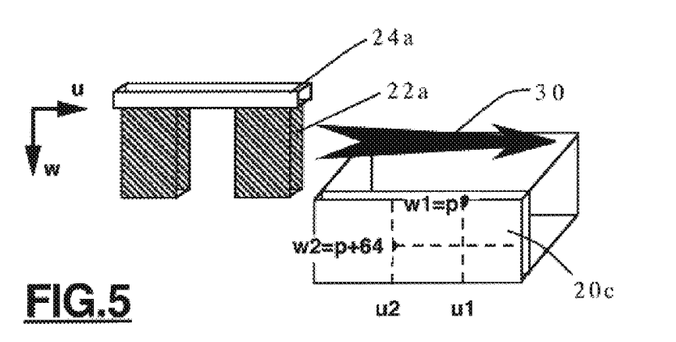
FIG. 5 is a schematic view of the detector 24a, the collimator 22a, and the object 20c containing the two point sources.
Figure 6:
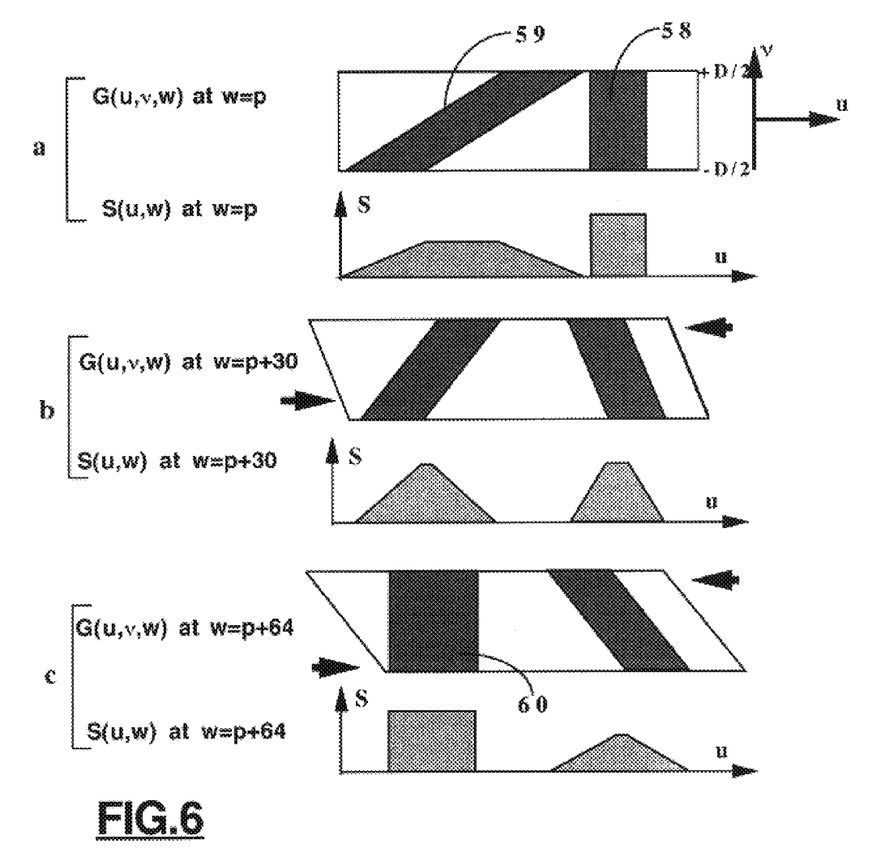
FIG. 6 is a set of graphs illustrating the raw acquisition G(u,v,w) and the data after shift and sum. The process has been done for three values of w: w=p (FIG. 6a) w=p+30 (FIG. 6b) and w=P+64 (FIG. 6c)

For the sake of clarity FIGS. 5 and 6 explain graphically the shift and sum process.

FIG. 5 represents for $\phi=0$, the collimator 22a and the detector 24a. The linear movement 30 is represented by an arrow and two point sources are represented as part of the object 20c. One point source is placed at the coordinate u1, w1=P the other at coordinate u2, w2=P+64. Where P is the depth of the collimator.

FIG. 6 represents the acquisition response $G(\chi,v,\phi)$, the data after the shift process $G(u,v,w)$ and after shift and sum $S(u,w)$. These last two functions are given for three values of reconstructed w. First for w=P (a) then w=P+30 (b) last w=P+64 (c). At w=P $G(u,v,w)$ equals $G(\psi,v, \phi)$ because the shift is null and $\phi=0$. The arrows in the subsequent $G(u,v,w)$ indicate the shift. The response $G(u,v,w)$ exhibits a rectangle shape 58 for the source u1 when w=P and a rectangle shape 60 for the source u2 when w=P+64. All the others responses present a parallelogram shape like 59. The depth of the source is easily coded with a high contrast in the acquisition.

All the reasoning has been made for $\phi=0$, but it applies to every angle $\phi$. After this process the equation system to solve is similar to a block toeplitz matrix, whose diagonal blocks represent the rectangle function of width: wD/P. (w: direction perpendicular to the detector, D: diameter of the collimator hole, P: depth of the collimator hole).

Figure 7:
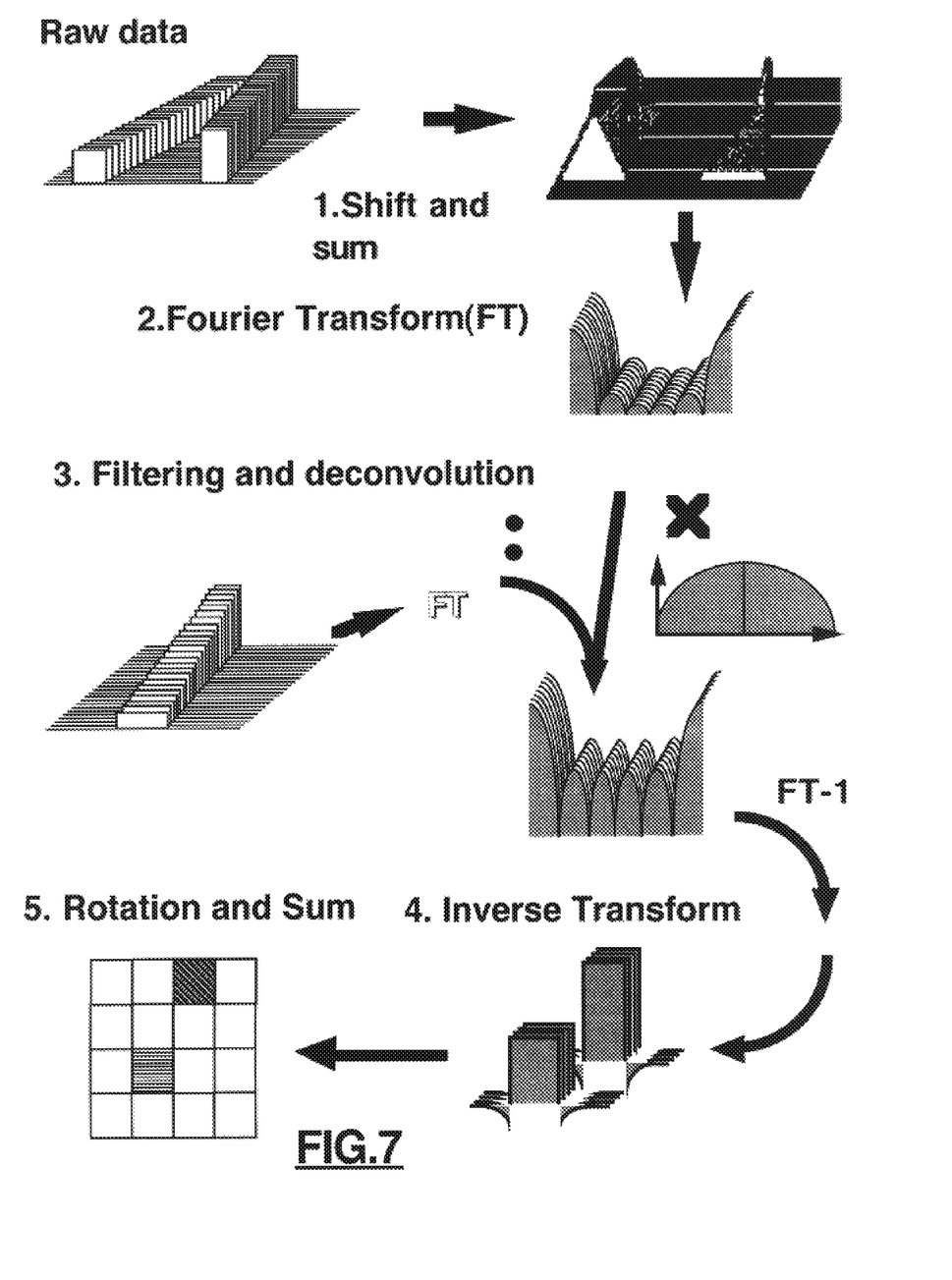
FIG. 7 is a flow chart of the whole tomographic reconstruction process for the high sensitivity gamma camera with linear scanning movement and orbital movement.

FIG. 7 gives the flow chart of a possible reconstruction algorithm for the high sensitivity radiation imaging system. The algorithm consequently performs:

1 Shift and sum

2 Fourier transform

3 Filtering and deconvolution.

4 Inverse Fourier transform

5 Rotation and sum

An iterative refinement can eventually be added to the process. The Fourier transform at stages 2 and 4 makes the algorithm faster and facilitates the filtering. The deconvolution at stage 3 uses a rectangle function of width wD/P. A parabolic filtering replaces the standard ramp filtering used in conventional tomographic reconstruction. The backprojection is here replaced by a simple sum after suitable rotation, because each entire u,w plane is reconstructed. Note here that in this reconstruction plane the process takes a full account of the source to detector distance (w).

One of the embodiments of the improvement concern the deconvolution stage. Consider the standard convolution equation:

$$S(u) = \int \rho(u-\xi) \Pi(\xi) d\xi = \rho \otimes \Pi$$

Where $\rho$ is the solution, $\Pi$ is the rectangle function and S is the data after shift and sum. In the Fourier domain the convolution is replaced by a simple multiplication and conversely the deconvolution process is replaced by a division.

Figure 8:
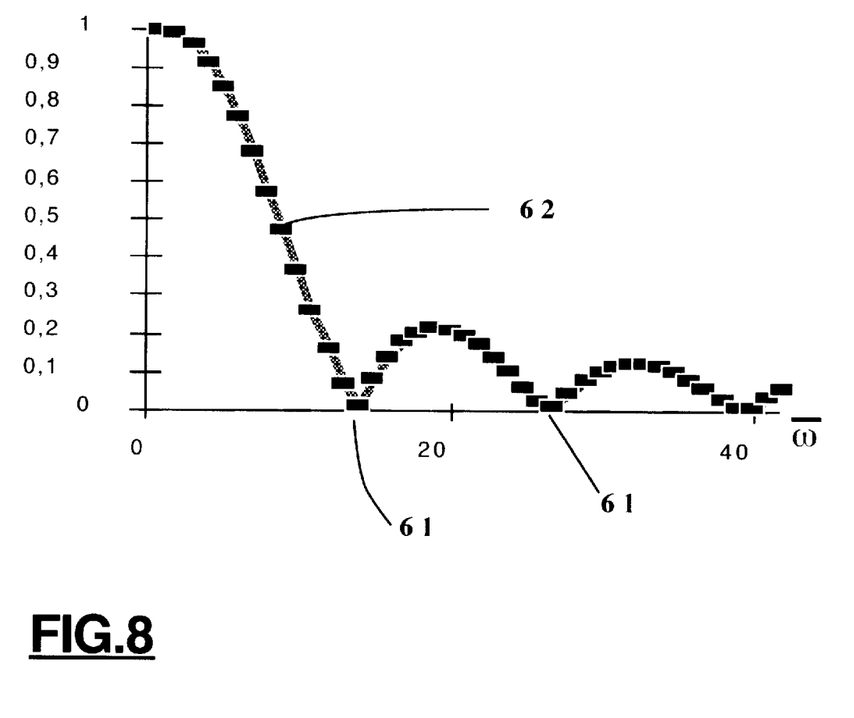
FIG. 8 is a graph of the modulus 62 of the Fourier transform of a rectangle function.

FIG. 8 represents the modulus 62 of the Fourier transform of a rectangle function. This function presents near zero values 61 which cause problems during the deconvolution process.

To avoid the near zero values occurring in the Fourier transform of the function $\Pi$, we propose to change the simple problem of deconvolution by a double problem of deconvolution with two rectangular functions $\Pi_A$ and $\Pi_B$. A collimator with two holes of different shape (for example different cross section) can be used for this purpose.

$$\begin{cases} S_A(u) = \int \varrho(u-\xi)\Pi_A(\xi)d\xi = \varrho \otimes \Pi_A \\ S_B(u) = \int \varrho(u-\xi)\Pi_B(\xi)d\xi = \varrho \otimes \Pi_B \end{cases}$$

Figure 9:
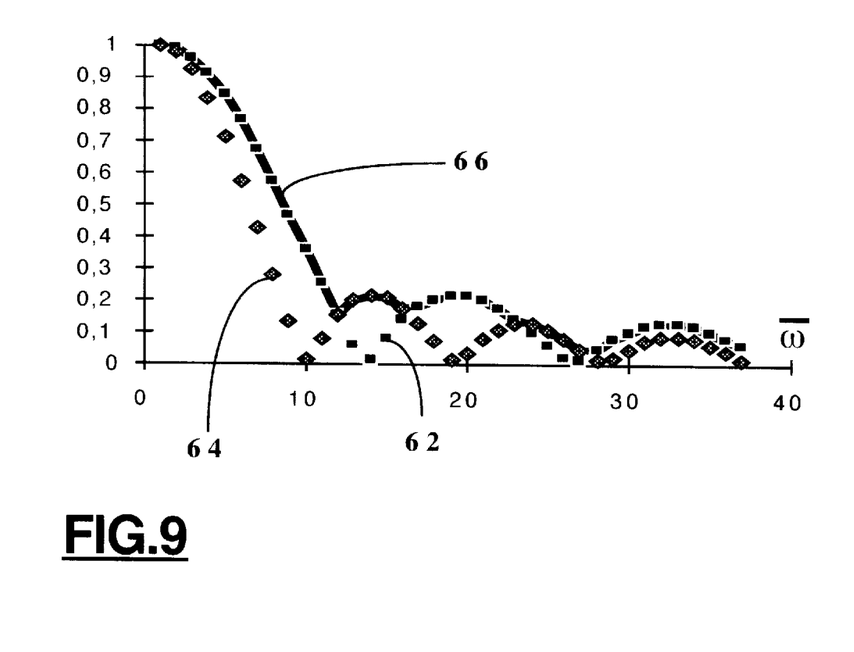
FIG. 9 is a graph of the modulus of the Fourier transform of two rectangle functions (62,64). The two rectangle function having different widths. The modulus 66 of the resulting kernel describe in the algorithm is also presented.

The following algorithm can be used in the Fourier space (variable $\overline{\omega}$): For All $\overline{\omega}$ If $\tilde{\Pi}_A(\varpi) > \tilde{\Pi}_B(\varpi)$ let $\tilde{\varrho}(\varpi) = \dfrac{\tilde{S}_A(\varpi)}{\tilde{\Pi}_A(\varpi)}$ If $\tilde{\Pi}_A(\varpi) < \tilde{\Pi}_B(\varpi)$ let $\tilde{\varrho}(\varpi) = \dfrac{\tilde{S}_B(\varpi)}{\tilde{\Pi}_B(\varpi)}$ FIG. 9 is a graph representing the modulus of the Fourier transform kernels $\Pi_A$ 62 and $\Pi_B$ 64. The application of the proposed algorithm divide the data by the maximum of both modulus that is by the curve represented by the black line 66 on the FIG. 9. A simple examination of the FIG. 9 shows that this curve avoids the near zero values of each curve 62 or 64. A dramatic increase in terms of signal to noise ratio has been obtained with this method. Other algorithms can be derived to benefit from the full set of data but the fast algorithm described herein demonstrates clearly the benefit obtained by this improvement. Obviously the combination of more than two signals is also possible giving a smaller but still interesting improvement.

Figure 10:
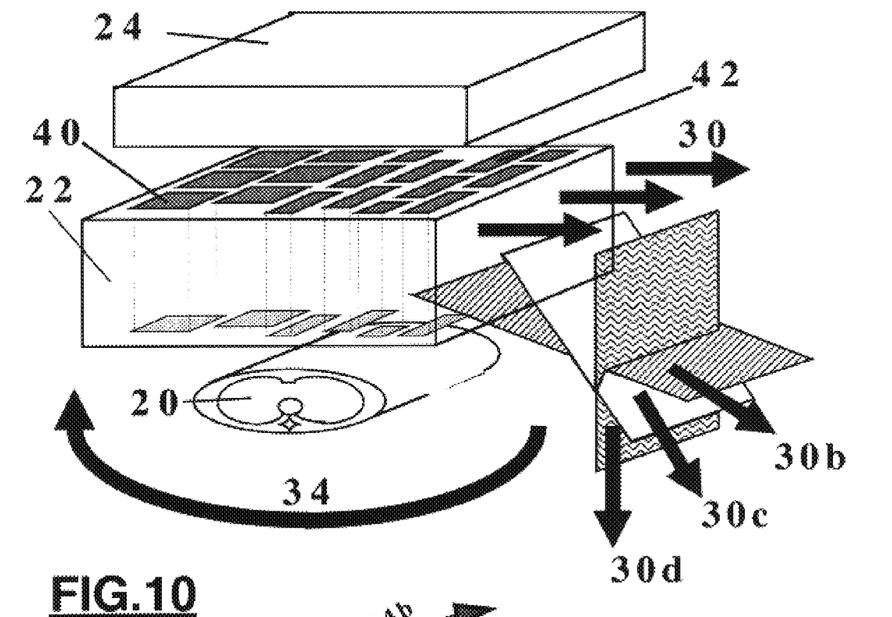
FIG. 10 is an exploded view of a possible arrangement for the invention with a linear scanning movement 30 perpendicular to the axis of rotation. The linear movement and a circular or orbital movement 34 are performed around the patient 20.

FIG. 10 represents an exploded view of a possible arrangement of the improvement. The patient 20 is represented next to the collimator 22 with two sets of holes of different shape for example 40 and 42. The detector 24 is slightly shifted in this exploded view. The gantry is not represented but a linear scanning movement 30 and an orbital or circular movement 34 are both represented. At each rotation step a scanning movement occurs (30b,30c, 30d). This is better explained on the FIG. 11.

Figure 11:
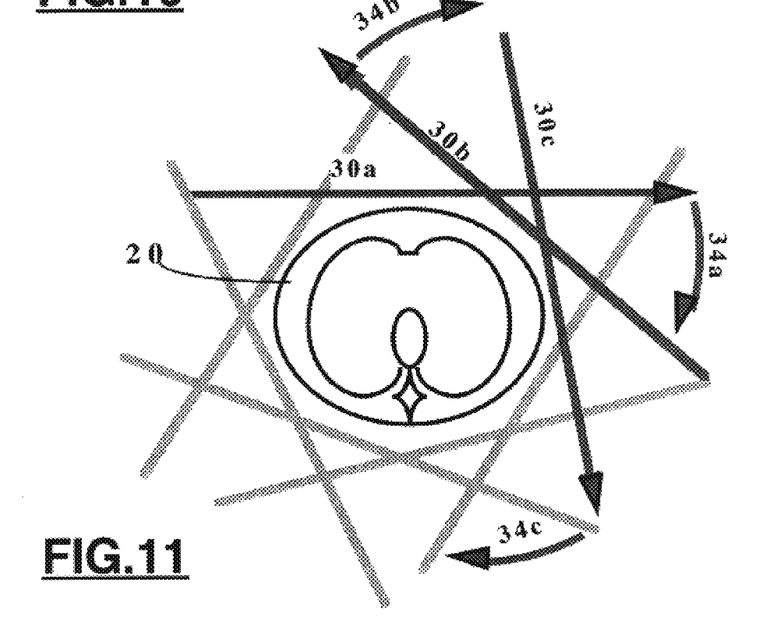
FIG. 11 is a possible sequence combining both linear and circular movement in an alternating way.

FIG. 11 is a view taken in the direction of the axis of rotation of FIG. 10. It depicts a possible sequence of the movement for the high radiation imaging system in the arrangement of FIG. 10. In this example the axis of rotation is perpendicular to a linear movement. The sequence begins by a linear movement 30a which is composed of several steps (depending on the resolution sought). Then a single step of circular movement 34a follows, then the second linear movement 30b takes place in the reverse direction, then the second circular step 34b follows, the third stage is described by 30c, 34c. The acquisition stops when a complete orbit is performed around the object. It is to be noted that the orbit does not necessarily need to be circular and elliptic movements are possible. In the same way a change in the order of the sequence does not alter the principle of the improvement (see FIG. 14).

Figure 12:
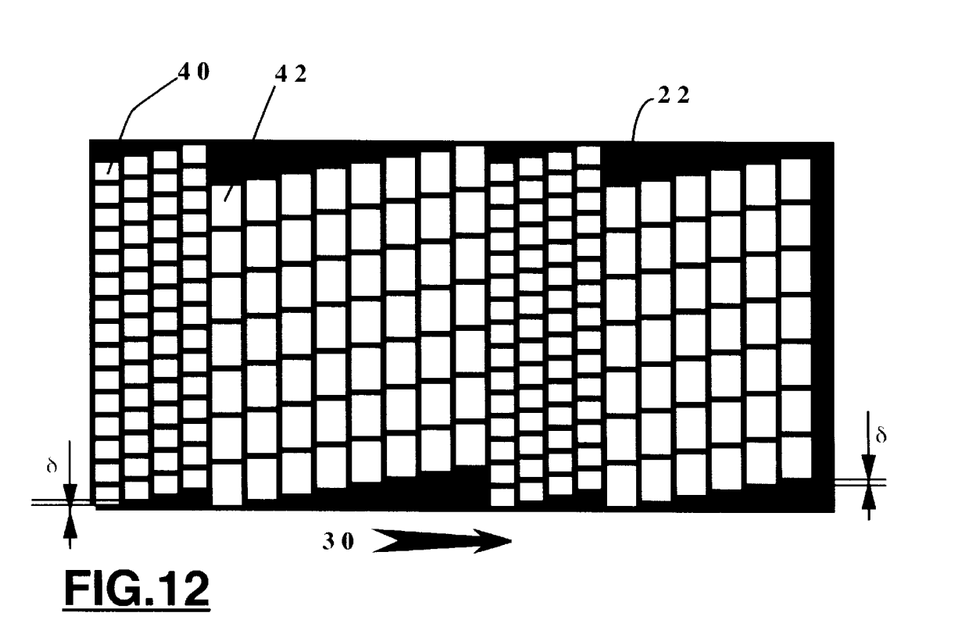
FIG. 12 is a view of a possible arrangement of two sets of rectangles holes (40 42) to form a complete collimator. The arrow 30 represents the direction of the linear scanning movement.

FIG. 12 shows a possible arrangement of two sets of holes (40 and 42) on the collimator 22 viewed by its entrance plane. The direction of the linear movement 30 is represented. The dimension of the scanning step $\delta$ equals the shift between two holes belonging to two adjacent columns. This arrangement in slanted rows ensures a complete set of data as described in the U.S. Pat. No. 5,448,073 (September 1995 Jeanguillaume). This arrangement is equivalent to a 2D scanning sequence giving a periodical lattice e.g. the centers of the openings had passed on the position of the corners of a tiling of squares of side $\delta$.

Figure 13:
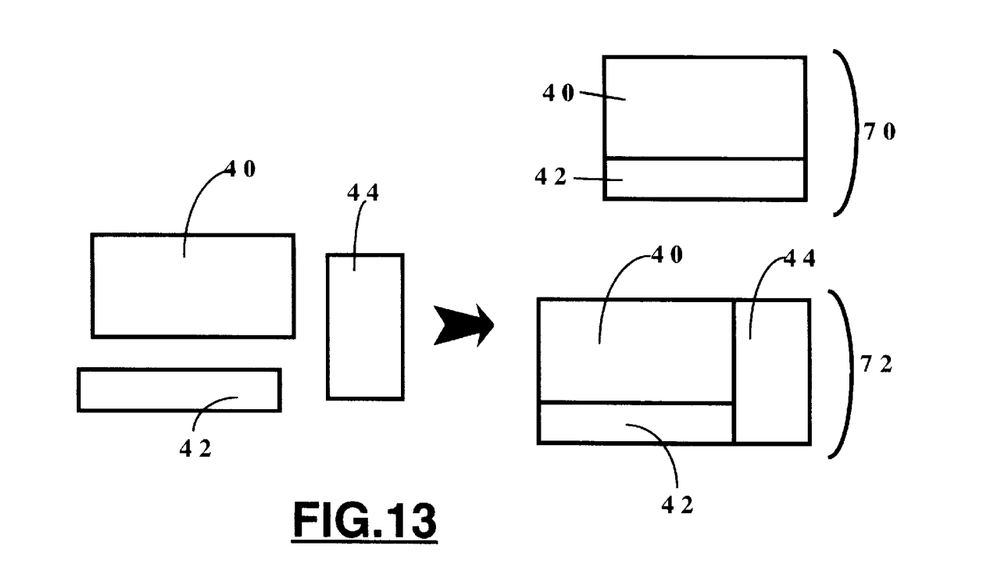
FIG. 13 is a schematic view aimed at demonstrating the way data provided from three different holes (40,42,44) may be assembled to form supplementary information.

FIG. 13 shows a possible arrangement for 3 holes or 3 sets of holes. The hole 40 could be chosen with the same length as the hole 42. This arrangement ensures a possible concatenation of the two holes 50. This concatenation 70 can be made at the processing time to ensure a new rectangle kernel. This third kernel is of interest because it can be combined with the former (40,42) to further eliminate the near zero values in the Fourier plane, as in FIG. 9.

In this arrangement the widths of the holes can also be combined. Let the width of the hole 40 plus the width of the hole 42 equal the width of the third hole 44. Then the combination of the three holes 72 can be made with the data giving an additional rectangle kernel for the deconvolution.

Figure 14:
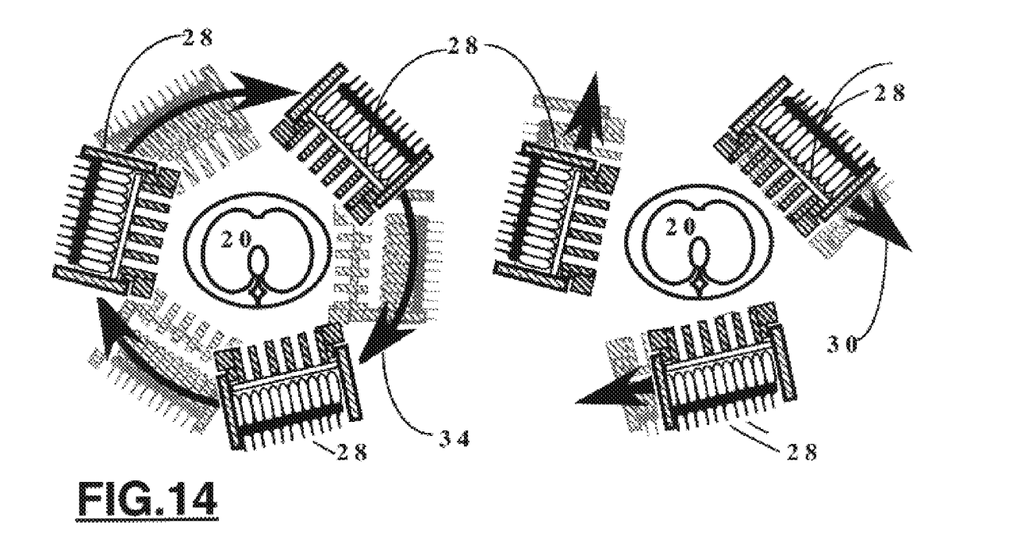
FIG. 14 is another possible arrangement of the invention where a complete circular movement takes place between each step of linear movement.

FIG. 14. represents a three headed camera. The patient 20 is surrounded by three camera heads 28. At least two sets of holes with two different shapes take place in the three collimators. This can be performed with holes of two (three) different diameters or depths. The purpose of FIG. 14 is to illustrate another possible sequence of acquisition. To simplify the description of the acquisition the three collimators are considered identical. It is to b e noted that two modes of acquisition can be used: step and shoot and continuous mode. The same applies in the conventional single photon emission computerized tomography (SPECT). Both modes will be described in this case beginning with the step and shoot mode. In the left hand side of FIG. 14 the three heads are involved in a circular movement 34. After a rotation of 120° (one third of 360°) a complete orbital acquisition has been performed, then a step of linear movement 30 can be carried out for the three heads (slightly exaggerated in the right hand side of FIG. 14). The second circular movement of 120° can be performed followed by the second step of linear movement and so on until the end of the linear movement has been reached. This sequence described in the step and shoot mode can easily be performed in the continuous mode. The two linear and circular movements are then carried out simultaneously. The only requirement is that the speed of the two movements matches the ratio 120° rotation per step of linear movement, although 180° per step would be required for a two headed camera with two identical collimators. Three hundred and sixty degrees per step would be required for a single headed camera or a camera with non identical collimators. In this example a linear movement is used which in combination with the arrangement of the hole is equivalent to a 2 dimensional (planar) movement. By the same token an inclination of the head by a small amount at each rotation with or without a change in the radius would produce the same effect.

Figure 15:
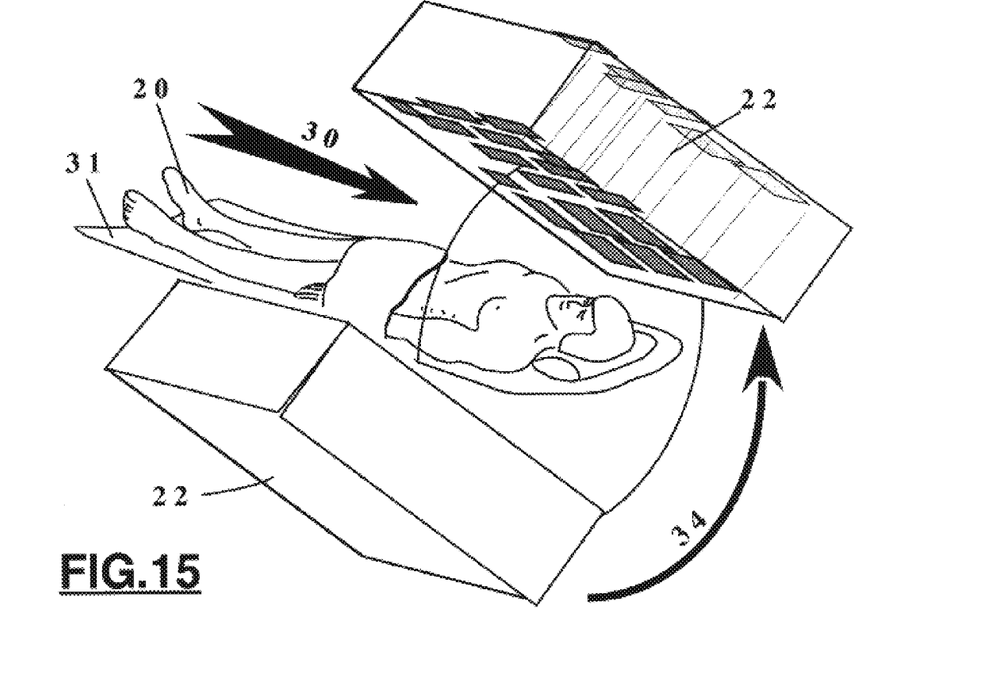
FIG. 15 is another possible arrangement of the invention where the source operates a linear movement while the camera head operates a continuous movement.

FIG. 15 describes another acquisition sequence well suited for a whole body tomographic acquisition, while the former description is more suited to a localized single organ tomographic acquisition (like brain or heart). In the FIG. 15 the patient 20 is represented as the collimators 22 for a double headed camera system. The complete camera heads are not represented. The acquisition is as follows: each time the camera heads performs a complete orbital movement 34, the examination table 31 performs a step of linear movement 30. In the collimator 22 the holes are arranged like FIG. 12. This sequence applies equally well in the continuous mode.

What is claimed is:

1. High sensitivity radiation imaging system aimed at providing sections of the three dimensional density of an object emitting radiation comprising:
   (a) a detector sensitive to the position of the impinging radiation having an intrinsic spatial resolution, the said detector converting the position of impinging radiation into electrical signals,
   (b) a collimator having an entrance face directed towards the object to be imaged, and an exit face placed in front of the detector,
   (c) a means for holding the source of radiation to map and for moving the said collimator and the said detector in a scanning movement, this movement is defined relative to the source, the said scanning movement having a step dimension of the order of the spatial resolution sought,
   (d) a means for conducting the said scanning movement, for storing the said electrical signals related to the position of the said collimator and the position of the said radiation impact, for processing the information thus stored in order to reconstruct the image of the said emitting object,
   the said collimator having at least two openings whose narrowest cross-section has a dimension larger than twice the intrinsic spatial resolution of the said detector, the improvement characterized in that the said collimator possesses at least two holes of different shapes, sizes or orientations resulting in different overlapping impulse functions in the Fourier space.

2. The radiation imaging system according to claim 1 wherein said openings have circular, hexagonal or rectangular cross sections and are placed in a compact arrangement.

3. The radiation imaging system according to claim 2 wherein said openings are frustoconical.

4. The radiation imaging system according to claim 2 wherein said different openings, are arranged on different sets, each set having a plurality of openings with the same shapes, sizes or orientations, in each set the said openings lie on mutually parallel straight lines, these straight lines making an angle with the direction of the said scanning movement such that the shift of the centers of two successive openings centered on the same straight line in the direction perpendicular to the direction of movement is substantially equal to the scanning step.

5. The radiation imaging system according to claim 4 wherein the said scanning movement is linear.

6. The radiation imaging system according to claim 5 wherein an additional orbital or circular movement around the object is added to the said linear movement.

7. The radiation imaging system according to claim 6 wherein the scanning movement is linear along the axes of the orbital or circular movement.

8. The radiation imaging system according to claim 6 wherein the said linear movement is tangential to the orbital movement.

9. The radiation imaging system according to claim 7 wherein the said detector is circular or polygonal around the object to be imaged.

10. The radiation imaging system according to claim 2 wherein the said openings differ by their depth.

11. The radiation imaging system according to claim 1 wherein at least three of the said openings have a cross section of parallelogram shape, the width of 2 of the said openings equals the width of the other third, and a similar relation applies for the length.

12. The radiation imaging system according to claim 1 wherein the said detector follows the collimator in its scanning movement.

13. The radiation imaging system according to claim 1 wherein the said detector is fixed.

14. The radiation imaging system according to claim 1 wherein the said scanning movement affects the direction of the axes of the openings of the collimator.

15. The radiation imaging system according to claim 1 wherein the said scanning motion result is that the centers of the openings describe a compact lattice in a 2D geometrical surface.

16. The radiation imaging system according to claim 12 wherein the system comprises a plurality of heads.

17. The radiation imaging system according to claim 1 comprising a detector of the semiconductor type.

18. The radiation imaging system according to claim 1 wherein the detector comprises a scintillating system having an entrance face place behind said collimator.

19. The radiation imaging system according to claim 1 wherein said processing means comprises means for applying a shift and sum algorithm, to all the stored information, through a shift of the information in a spatial direction parallel to the direction of the collimator scanning movement, and a sum of the information collected in the said openings.

20. The radiation imaging system according to claim 19 wherein said processing means comprises a means for deconvolving the function corresponding to the said information, after shift and sum, with a top-hat function depending on the source to detector distance, this processing resulting in a tomographic reconstruction.

* * * * *